United States Patent
Kau et al.

(10) Patent No.: US 8,809,808 B2
(45) Date of Patent: Aug. 19, 2014

(54) STIMULATED EMISSION-BASED OPTICAL DETECTION SYSTEM

(75) Inventors: Fu-Jen Kau, Taipei (TW); Po-Yen Lin, Taipei (TW)

(73) Assignee: National Yang Ming University, Taipei (TW)

( * ) Notice: Subject to any disclaimer, the term of this patent is extended or adjusted under 35 U.S.C. 154(b) by 914 days.

(21) Appl. No.: 12/971,998

(22) Filed: Dec. 17, 2010

(65) Prior Publication Data
US 2012/0112094 A1    May 10, 2012

(30) Foreign Application Priority Data
Nov. 19, 2010   (TW) ................. 99140095 A

(51) Int. Cl.
| | | |
|---|---|---|
| *G21K 5/00* | (2006.01) | |
| *G01J 1/58* | (2006.01) | |
| *G01N 21/63* | (2006.01) | |
| *G01J 3/44* | (2006.01) | |
| *G01N 21/17* | (2006.01) | |

(52) U.S. Cl.
CPC . *G01J 3/44* (2013.01); *G01N 21/63* (2013.01); *G01N 2021/1793* (2013.01)
USPC ..................... 250/458.1; 250/459.1

(58) Field of Classification Search
USPC ............................ 250/458.1, 459.1
See application file for complete search history.

(56) References Cited

U.S. PATENT DOCUMENTS

| | | | | |
|---|---|---|---|---|
| 5,058,117 | A * | 10/1991 | Shoshan et al. | 372/3 |
| 5,646,411 | A * | 7/1997 | Kain et al. | 250/458.1 |
| 5,731,588 | A * | 3/1998 | Hell et al. | 250/458.1 |
| 7,599,115 | B2 * | 10/2009 | Gugel | 359/385 |
| 7,616,307 | B2 * | 11/2009 | Murtagh et al. | 356/326 |

* cited by examiner

*Primary Examiner* — David Porta
*Assistant Examiner* — Mindy Vu
(74) *Attorney, Agent, or Firm* — Muncy, Geissler, Olds & Lowe, P.C.

(57) ABSTRACT

The present invention provides an optical detection system comprising an illumination unit and a detection unit. The illumination unit comprises two laser beams of two different wavelengths. One beam is used to excite targeted molecules in a sample to their excited states. The other beam is used to induce the excited molecules in the sample to generate a stimulated emission signal. The stimulated emission signal can be used for long-distance detection due to its coherent property. Its extraction from the detection unit can be realized by demodulating the second beam's intensity change.

19 Claims, 4 Drawing Sheets

STIMULATED EMISSION-BASED OPTICAL DETECTION SYSTEM

PRIORITY CLAIM

This application claims the benefit of priority to Taiwanese Patent Application 099140095, filed Nov. 19, 2010; herein incorporate by reference in its entirety.

BACKGROUND OF THE INVENTION

1. Field of the Invention

The invention relates to a stimulated emission based optical detection system, and more specifically, to the optical detection system used for long-distance signal detection.

2. Description of Related Art

Various optical detection and imaging techniques are widely used for biomedical detection. Optical imaging techniques now used for biomedical imaging include fluorescence and nonlinear optics techniques. In nonlinear optical imaging, optical signals produced by the nonlinear optical interactions of photons and samples are detected and used to reconstruct images of samples.

Nonlinear optical techniques claim extended depth of field by using longer wavelength, which is useful when targets under biological tissues are difficult to detect because of the limited penetration of visible light. The technique is also effective for imaging the inner objects of light absorption materials.

Conventional methods of using optical signals for biomedical detection include polarization, absorption, fluorescence, Raman scattering, second-harmonic generation (SHG), third-harmonic generation (THG), and coherent anti-stokes Raman scattering (CARS), and other nonlinear optical signals. One example is fluorescence spectroscopy, which is widely used for measuring photoluminescence to detect changes in molecular energy. In the single-photon excitation mechanism, the fluorescent molecule emits long-wavelength photons after irradiation with short-wavelength photons. The emitted photons 110 are usually isotropic, as FIG. 1. Therefore, to improve detection efficiency, lenses with high numerical aperture which could provide broad solid angles are often used to collect fluorescent signals.

The above optical signal strength is usually very weak when compared to incidental light. To detect weak signals effectively, a highly sensitive optical detector or a high-intensity incident light source is needed. However, highly sensitive optical detectors are very expensive, and high-intensity incident light sources can easily damage samples. Another way to improve detection efficiency is to increase the lens aperture to enhance signal collection. Nonetheless, a high numerical aperture lens is usually limited by short its working distance. Overcoming the problem of detecting weak signals effectively at long detection distance is an important issue.

BRIEF DISCRIPTION OF THE INVENTION

The optical detection system of the invention comprises mainly of three units: an illumination unit, an optical unit, and a detection unit.

The illumination unit includes an excitation beam and a stimulation beam. The excitation beam is provided to excite targeted molecules in a sample to their excited states. The stimulation beam is provided to induce the excited molecules in the sample to generate a stimulated emission signal.

The optical unit is provided to control the integration, split or direction of the excitation beam, the stimulation beam and the stimulated emission signal. The optical unit includes a beam splitter, a scanner, a collecting optics, and a back-reflector.

The excitation beam and the stimulation beam is combined and steered by the beam splitter. The two beams are then collimated into a scanner. The projection optics then ensures the overlapping of the excitation beam and stimulation beam over the targeted area in the sample.

After being reflected via the back-reflector, the stimulated emission signal is directed into the detection unit. The detection unit then analyzes the stimulated emission signal to determine the strength of the weak signals due to the modulation of the excitation beam.

The detection unit includes a beam splitter, a band-pass filter, a collecting optics, a photo-detector, and a lock-in amplifier.

After being reflected via the back-reflector, the stimulated emission signal is decoupled from the excitation beam via the beam splitter and is passed through the band-pass filter. The stimulated emission signal is collected into the photo-detector via the collecting optics. After receiving optical signals, the photo-detector will transform these optical signals to amplified electric signals.

The lock-in amplifier is used to extract the stimulated emission signal from the photo-detector by demodulating the signal from the stimulation beam.

Because of the high coherence of the stimulated emission, the optical detection system is capable of long-distance signal detection. It can overcome the collection efficiency limitations due to numerical aperture and addresses the problem of short working distance between the sample and the high NA optics.

DETAILED DESCRIPTION OF THE EMBODIMENTS

The optical detection system capable of long-distance detection of weak signals in the proposed invention solves the problems of prior art. The weak signals comprise all types, and in the embodiment, fluorescent signals are taken as examples. The weak signals are not limited fluorescent signals in the invention.

A number of ways are provided for a fluorescent molecule being exited to an exited state from its ground states. These ways include non-radiative, spontaneous transition, stimulated emission, and energy transfer methods.

The invention detects the energy level transition of the fluorescent molecules by analyzing the stimulated emission signal. Since the stimulated photons are of high coherence, they are also highly directional. As a result, the optical detection system in this invention overcomes the limitations of numerical aperture in collecting weak signals efficiently and further solves the problem of short working distance between the sample and the objective lens.

Further, other weak signals, such as Raman signals, can also be detected similarly by the way of the stimulated emission so as to be called stimulated Raman. Raman signals reflect molecule identity. There is no need for fluorescence labeling. The advantage is the conversion of low-coherence emissions into high-coherence stimulated signals.

Figure 1:
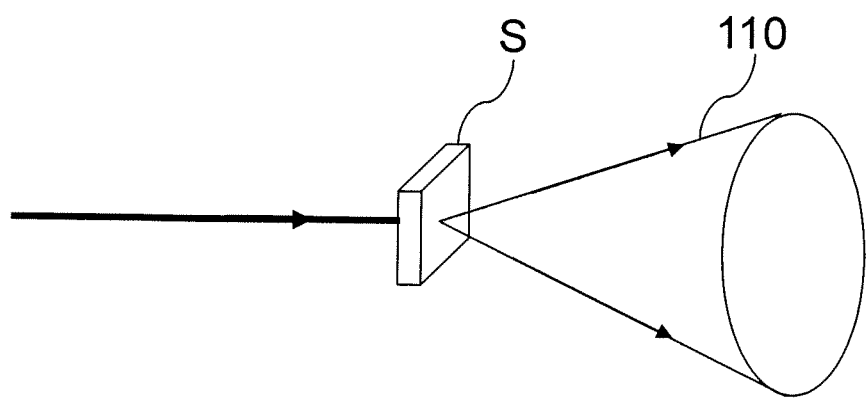
FIG. 1 is a schematic diagram showing the typical spatial distributions of fluorescence in the forward direction after the incident excitation.
Figure 2:
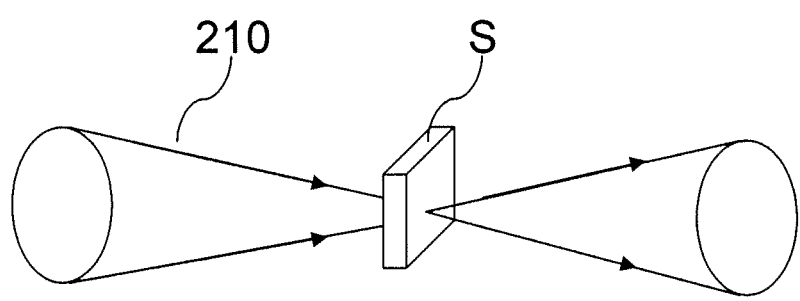
FIG. 2 is a schematic showing the excitation beam exciting molecules in a sample to their excited states, and the emitted photons from the excited molecules are isotropic.

FIG. 2 is a schematic showing the excitation beam provided to exciting targeted molecules in the sample to their excited states, and the emitted photons from the excited molecules are isotropic. The direction of light propagation is shown with arrows.

Figure 3:
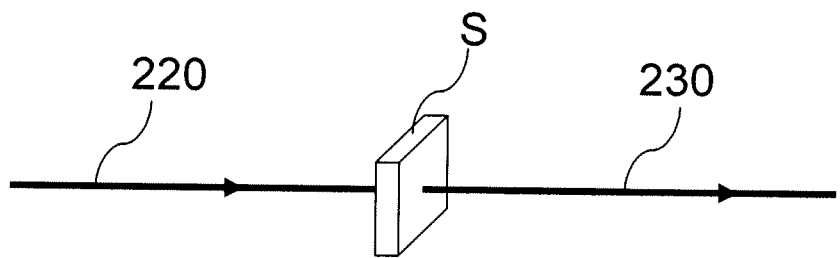
FIG. 3 is a schematic showing the stimulation beam induced the photons of the excited molecules of the sample to generate a stimulated emission signal.

FIG. 3 is a schematic diagram showing the stimulation beam induced the photons of the excited molecules in the sample to generate a stimulated emission signal.

Figure 4:
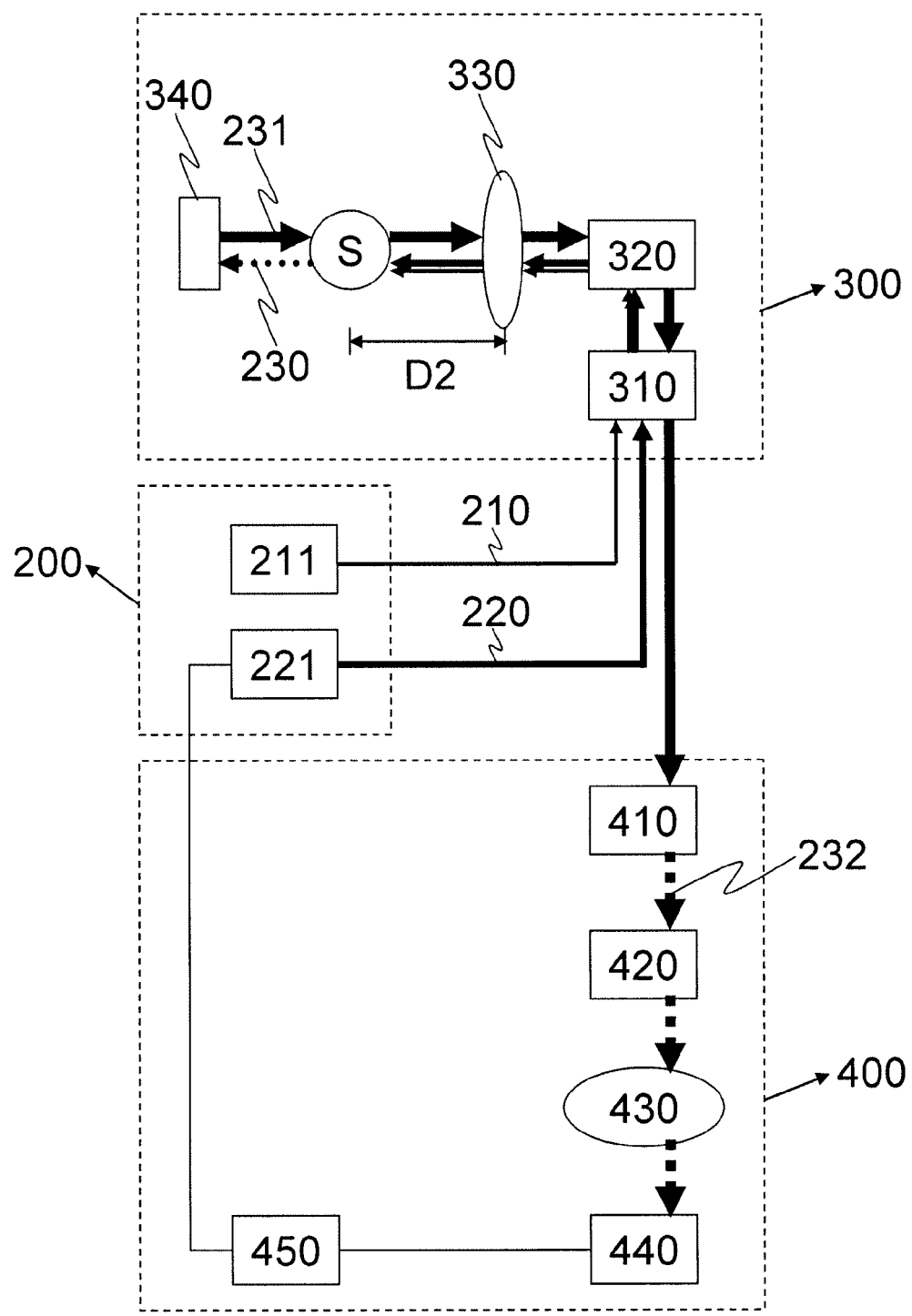
FIG. 4 is a schematic of the optical detection system of this invention.

FIG. 4 is a schematic showing the optical detection system in the invention. The optical detection system includes three main units: an illumination unit 200, an optical unit 300 and a detection unit 400.

The illumination unit 200 includes an excitation beam 210 and a stimulation beam 220. The excitation beam 210 is provided to excite molecules in the sample S to their excited states. The stimulation beam 220 is provided to induce the excited molecules in the sample S to generate a stimulated emission signal 230. Photons of the stimulated emission signal 230 and photons of the stimulation beam 220 are coherent with each other.

In the embodiment, the excitation beam 210 and the stimulation beam 220 are optical beams. One only needs to ensure that the excitation beam 210 and the stimulation beam 220 overlap over the targeted area in the sample S.

In the embodiment, the sample S used was a stack of two quartz glass plates with a random distribution of Rhodamine 6G in between. The below parameters of wavelength and frequency are used for Rhodamine 6G Different parameters of wavelength and frequency may be required to work with a different sample S. The invention is not limited to these parameters of wavelength and frequency.

The excitation beam 210 is from a continuous wave laser with a wavelength of 500 nm to 550 nm. In the preferred embodiment, the first excitation beam 210 is a continuous-wave laser beam with a wavelength of 532 nm, but other beam types are possible. Further, the intensity modulation frequency of the excitation beam 210 is adjusted to 30 kHz to 40 kHz through a frequency modulator 211. The 36 kHz frequency of the first excitation beam 210 is also a preferred, but not required, embodiment.

The second stimulation beam 220 is from a laser of wavelengths between 560 nm and 580 nm. A wavelength of 570 nm is a preferred, but not required, embodiment.

In the above optical detection system of the invention, photons of the stimulated emission signal 230 and photons of the stimulation beam 220 are coherent and highly directional. Besides, the optical unit 300 is provided to control the integration, split or direction of the excitation beam 210, the stimulation beam 220, and the stimulated emission signal 230. The optical unit 300 includes a beam splitter 310, a scanner 320, a collecting optics 330, and a back-reflector 340.

The integration, split or direction of the excitation beam 210 and the stimulation beam 220 are controlled by the beam splitter 310. The excitation beam 210 and the stimulation beam 220 are then collimated into the scanner 320. The collecting optics 330 then ensures that the excitation beam 210 and the stimulation beam 220 are overlapped over the targeted area on the sample. The preferred, but not required, embodiment of the collecting optics 330 is a single plano-convex collimation lens with a 400 mm focal length, and the collecting optics 330 further can be a convex lens, a grin lens, a concave mirror or a Fresnel zone plate. The beam splitter 310 can be a polarization beam splitter, a PLC splitter or a grating.

The collecting optics 330 avoids astigmatism caused by the collinear coupling of the excitation beam 210 with the stimulation beam 220 by ensuring that they have the same focal point for sample S. In the preferred embodiment, the collecting optics 330 includes a long working distance D2 to increase the detection distance. The stimulation beam 220 then induces the excited molecules in the sample S to generate the stimulated emission signal 230.

The stimulated emission signal 230 is reflected by the back-reflector 340 of the optical unit 300 along the same direction. The back-reflector 340 is a short-pass mirror or filter, being a dichroic short-pass mirror in the preferred embodiment, but not limited to be one. The back-reflector 340 also can be a dielectric mirror, a grating, or spectrally dispersive elements. The back-reflector 340 only reflects beams with wavelengths longer than 540 nm. Therefore, the signal reflected by the back-reflector 340 contained mostly the stimulated emission signal 231 with a specific wavelength.

Then, the detection unit 400 is provided to detect the reflected stimulated emission signal 231 to determine the intensity change in weak signals from the excited sample S. The detection unit 400 includes a beam splitter 410, a band-pass filter 420, a collecting optics 430, a photo-detector 440, and a lock-in amplifier 450.

After being reflected via the back-reflector 340, the reflected stimulated emission signal 231 is decoupled from an estimative signal 232 via the beam splitter 410 and then converged by the band-pass filter 420. The preferred, but not required, embodiment for the band-pass filter 420 is a long-pass filter. The band-pass filter 420 is provided to filter out unnecessary wavelengths and can also integrate different beams. In the above embodiment, the back-reflector 340 only reflects the beams with wavelengths longer than the specified wavelength. The back-reflector 340 therefore reflects most beams with long wavelength. The estimative signal 232 is further filtered via the band-pass filter 420 to select specific wavelength.

The estimative signal 232 is collected to the photo-detector 440 via the collecting optics 430. Optical signals received by the photo-detector 440 are transformed into electric signals. The photo-detector 440 then further amplifies and transforms the electric signals into digital signals. The photo-detector 440 further can be a photomultiplier tube, an avalanche photodiode or a photodiode.

The lock-in amplifier 450 is used to extract the stimulated emission signal 230 from the photo-detector 440 by demodulating the signal from the stimulation beam 220.

To sum up, the optical detection system in the invention provides the excitation beam 210 to excite targeted molecules in the sample S, and the stimulation beam 220 is provided to induce the excited molecules in the sample S to generate the stimulated emission signal 230, and wherein photons of the stimulated emission signal 230 and photons of the second stimulation beam 220 are coherent with each other.

Because of the need to measure intensity change in the stimulated emission signal 230, the lock-in amplifier 450 is used. After the excitation beam 210 is modulated to excite sample S, the stimulation beam 220 is used to induce stimulated emission from the excited sample S. Finally, the lock-in amplifier 450 is provided to demodulate and measure the estimative signal 232 The invention detects the energy level transition of the fluorescent molecules by analyzing the stimulated emission signal. Since the stimulated photons are of high coherence, they are also highly directional. As a result, the optical detection system in this invention overcomes the limitations of numerical aperture in collecting weak signals efficiently and further solves the problem of short working distance between the sample and the objective lens.

The long-distance signal detection capability of the invention has potential use in medical imaging or environmental monitoring. The optical detection system of the invention has a greater and farther imaging field so as to increase the working distance between the sample S and the object lens, even up to several meters or beyond.

Although the present invention has been described in considerable detail with reference to certain preferred embodiments thereof, this disclosure does not limit the scope of the invention. Persons with ordinary skill in the art may make various modifications and changes without departing from the scope. Therefore, the scope of the appended claims should not be limited to the description of the preferred embodiments described above.

What is claimed includes:

1. An optical detection system, comprising:
    an illumination unit, comprising:
        an excitation beam, being modulated at a selected frequency, to excite targeted molecules in a sample to their excited states; and
        a stimulation beam, to induce the excited molecules in the sample to generate a stimulated emission signal, wherein photons of the stimulated emission signal are in coherence with photons of the stimulation beam; and
    a detection unit, comprising:
        a photo-detector, to detect a signal from the sample, and
        a lock-in amplifier demodulates a electronic signal from the photo-detector with the selected frequency, to distinguish the stimulated emission signal from the stimulation beam for measuring the change of the intensity of the stimulated emission signal.

2. The optical detection system according to claim 1, further comprising an optical unit for controlling the integration, split or direction of the excitation beam, the stimulation beam and the stimulated emission signal.

3. The optical detection system according to claim 2, wherein the optical unit comprises a beam splitter to control the integration, split or direction of the excitation beam and the stimulation beam.

4. The optical detection system according to claim 3, wherein the optical unit comprises a scanner.

5. The optical detection system according to claim 4, wherein the optical unit comprises a collecting optics to collect the optical signal and to project the excitation beam and the stimulation beam to the same spot.

6. The optical detection system according to claim 5, wherein the collecting optics can be a convex lens, a grin lens, a concave mirror or a Fresnel zone plate.

7. The optical detection system according to claim 3, wherein the beam splitter can be a dichroic beam splitter, a polarization beam splitter, a PLC splitter or a grating.

8. The optical detection system according to claim 1, wherein the optical unit comprises a back-reflector to reflect the stimulated emission signal.

9. The optical detection system according to claim 8, wherein the back-reflector is a short-pass filter, such as a dielectric mirror, a grating, or spectrally dispersive elements.

10. The optical detection system according to claim 1, wherein the excitation beam and the stimulation beam are optical beams.

11. The optical detection system according to claim 10, wherein the excitation beam is able to excite the targeted molecules in the sample to their excited states.

12. The optical detection system according to claim 10, wherein the stimulation beam is able to induce the excited molecules in the sample to generate the stimulated emission signal.

13. The optical detection system according to claim 1, wherein the detection unit further comprises a beam splitter.

14. The optical detection system according to claim 13, wherein the beam splitter can be a dichroic beam splitter, a polarization beam splitter, a PLC splitter or a grating.

15. The optical detection system according to claim 1, wherein the detection unit further comprises a band-pass filter.

16. The optical detection system according to claim 15, wherein the band-pass filter is a long-pass one.

17. The optical detection system according to claim 1, wherein the detection unit further comprises a collecting optics.

18. The optical detection system according to claim 17, wherein the collecting optics can be a convex lens, a grin lens, a concave mirror or a Fresnel zone plate.

19. The optical detection system according to claim 1, wherein the photo-detector can be a photomultiplier tube, an avalanche photodiode, or a photodiode.

* * * * *